US010506819B2

(12) United States Patent
Schoeppe et al.

(10) Patent No.: US 10,506,819 B2
(45) Date of Patent: Dec. 17, 2019

(54) LOW-FAT WATER-IN-OIL EMULSION

(71) Applicant: Cargill, Incorporated, Wayzata, MN (US)

(72) Inventors: Arnulf Schoeppe, Hamburg (DE); Daniel Steiger, Pinnebreg (DE); Johan Guillaume Lucien Steyls, Tildonk (BE); Susanne Tirok, Hamburg (DE); Pauline Van Eesbeek, Neder-Over-Heembeek (BE)

(73) Assignee: Cargill, Incorporated, Wayzata, MN (US)

(*) Notice: Subject to any disclaimer, the term of this patent is extended or adjusted under 35 U.S.C. 154(b) by 110 days.

(21) Appl. No.: 15/557,975

(22) PCT Filed: Mar. 17, 2016

(86) PCT No.: PCT/US2016/022824
§ 371 (c)(1),
(2) Date: Sep. 13, 2017

(87) PCT Pub. No.: WO2016/149477
PCT Pub. Date: Sep. 22, 2016

(65) Prior Publication Data
US 2018/0055065 A1   Mar. 1, 2018

(30) Foreign Application Priority Data
Mar. 18, 2015   (EP) ..................................... 15159614

(51) Int. Cl.
*A23D 7/01* (2006.01)
*A23J 7/00* (2006.01)
*A23L 29/10* (2016.01)

(52) U.S. Cl.
CPC .............. *A23D 7/013* (2013.01); *A23D 7/011* (2013.01); *A23J 7/00* (2013.01); *A23L 29/10* (2016.08);
(Continued)

(58) Field of Classification Search
CPC ......... A23D 7/011; A23D 7/013; A23L 27/60; A23L 29/10; A23G 3/36; A23J 7/00;
(Continued)

(56) References Cited

U.S. PATENT DOCUMENTS 9,468,896 B2 * 10/2016 Schoeppe .............. A23D 7/011
2013/0003670 A1   1/2013 Li
(Continued)

FOREIGN PATENT DOCUMENTS

EP   0870840 A2   10/1998
EP   0997074 A1   5/2000
EP   0997075 A1   5/2000

OTHER PUBLICATIONS

The Proceedings of the Conference Food Organized by the Food Chemistry Group of the RSC held on Apr. 3-6, 2000 in Potsdam, Germany. 2001, the Royal Society of Chemistry, Ca mbridge, UK, XP002744235, ISBN: 085404-850-2, pp. 134-134.
(Continued)

*Primary Examiner* — Cephia D Toomer

(57) ABSTRACT

The present invention relates to a low-fat water-in-oil (W/O) emulsion comprising a fat phase in an amount of at most 60 wt % relative to the total weight of the emulsion, an aqueous phase dispersed within the fat phase and an emulsifier composition, said emulsifier composition comprising an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the
(Continued)

total weight of the emulsifier composition and wherein the emulsifier composition is characterized by a weight ratio R of at most 65%, the ratio R being defined as (1) wherein PC+PI+PE+PA is the sum of the individual weights of the respective constituents of the AI component and AI is the total weight of the AI component.

14 Claims, 1 Drawing Sheet

(52) U.S. Cl.
CPC ..... *A23V 2002/00* (2013.01); *A23V 2200/222* (2013.01); *A23V 2250/184* (2013.01)

(58) Field of Classification Search
CPC .............. C07F 9/106; A23V 2200/222; A23V 2250/184; A23V 2002/00
See application file for complete search history.

(56) References Cited

U.S. PATENT DOCUMENTS

| | | |
|---|---|---|
| 2014/0066623 A1 | 3/2014 | Steitz et al. |
| 2014/0066632 A1 | 3/2014 | Sharpless et al. |

OTHER PUBLICATIONS

"Lecithin" In: Mark et al: "Encyclopedia of Chemical Technology, vol. 14" Jan. 1, 1978 (Jan. 1, 1978), Kirk-Othmer Encyclopedia of Chemical Technology. Alkoxides, Metal, to Antibiotics (Peptides), New York, Wiley & Sons, US, pp. 250-269, XP002130043.

* cited by examiner

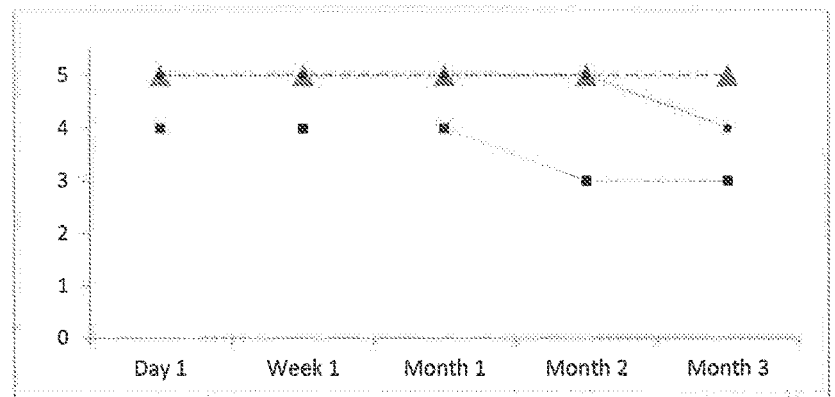
FIG 1.1
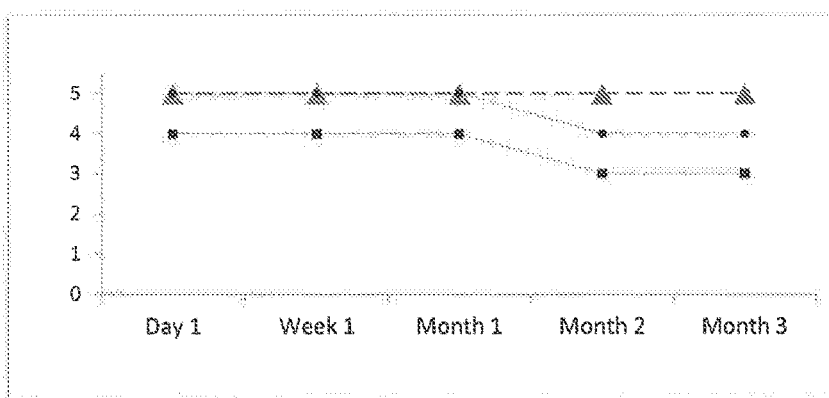
FIG 1.2
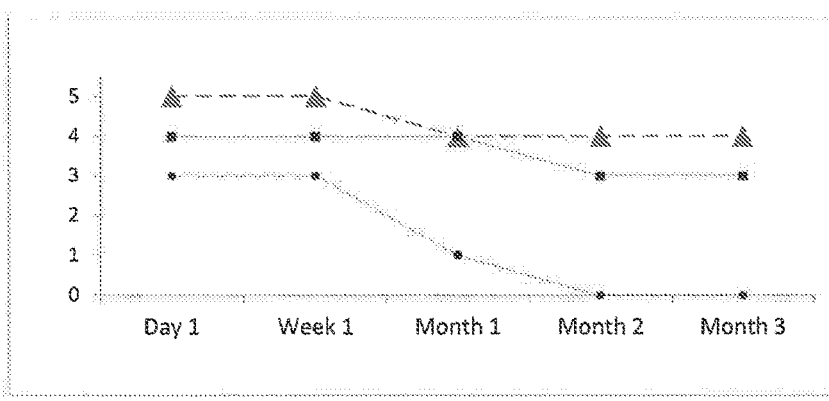
FIG 1.3

LOW-FAT WATER-IN-OIL EMULSION

CROSS REFERENCE TO RELATED APPLICATIONS

This application is a national phase application of PCT/US2016/022824, filed 17 Mar. 2016, entitled LOW-FAT WATER-IN-OIL EMULSION, which claims the benefit of priority to European Application No. 15159614.5 filed 18 Mar. 2015, entitled LOW-FAT WATER-IN-OIL EMULSION, which are hereby incorporated by reference in their entirety.

FIELD OF THE INVENTION

The invention relates to a low-fat water-in-oil (W/O) emulsion and its use in making food products. The invention further relates to food products comprising thereof.

BACKGROUND OF THE INVENTION

An emulsion is a composition containing a stable mixture of two immiscible phases, in which droplets of one phase are dispersed throughout the other phase. A typical example of an emulsion is a water-in-oil (W/O) emulsion wherein a certain content of water in a form of water droplets is uniformly dispersed throughout a lipid content that forms a continuous lipid phase. For instance, WO 2014/066632 discloses lipid-based W/O emulsions wherein the lipid content may vary from 1 to 99 wt %, Lipids may include waxes, sterols, fat-soluble vitamins (such as vitamins A, D, E, and K), monoglycerides, diglycerides, triglycerides, phospholipids, fats and others. Examples of lipids suitable for use in the W/O emulsions of WO 2014/066632 include vegetable or animal derived oils.

W/O emulsions where the lipid is a fat are typically used to manufacture various food products such as spreads, e.g. margarine. W/O emulsions can also be used as a precursor to prepare water-in-oil-in-water (W/O/W) or oil-in-water-in-oil (O/W/O) emulsions, which in turn may be used to make food products containing thereof, such as mayonnaise and dressings. For low fat W/O emulsions, i.e emulsions having an increased amount of water, the stability thereof may become problematic especially when the fat content drops below 60 wt % and particularly below 40 wt %. Food products containing low-fat W/O emulsions may be deleteriously affected by the emulsion's instability, e.g. experiencing flocculation, creaming, coalescence, and/or Ostwald ripening, which in turn may negatively influence their aspect, quality and/or mouthfeel behaviour. In order to stabilize low-fat W/O emulsions a number of strategies were developed.

One method to stabilize a low-fat W/O emulsion is to use special solid fat compositions as the fat phase thereof. EP 1 492 410; WO 2011/108919; and WO 2014/005797 contain disclosures of various solid fat mixtures used to stabilize low-fat W/O emulsions. However, solid fats typically contain an increased concentration of saturated fatty acids (SAFA) which are considered non-healthy as they are a known risk factor for cardiovascular health.

Another method to stabilize low-fat W/O emulsions is with the help of emulsifiers; and many effective emulsifiers are known such as esters of fatty acids, salts of fatty acids, lactylates, glycerol esters, polyglycereol esters of fatty acids, polyglycerol esters of polycondensed fatty acids of castor oil, fatty acid monoglycerides, fatty acid diglycerides, acetylated monoglycerides, calcium stearoyl dilaciate and lecithin. However, for achieving optimum stability in low-fat W/O emulsions, powerful emulsifiers need to be used in order to compensate for the reduced fat content (and hence increased water content). One of the few known emulsifiers able to effectively stabilize a low-fat W/O emulsion is polyglycerol polyricinoleate (PGPR), typically used in combination with a monoglyceride, a diglyceride and/or lecithin. EP-A-968,655; EP-B-1343384 and US2009/0029025 disclose for example low-fat W/O emulsions stabilized with PGPR. The use of PGPR (identified as E476) and mono- or di-glycerides (identified as E471) may bring however a number of disadvantages. The low-fat W/O emulsions containing such powerful emulsifiers are so stable that their melting behaviour is affected. In particular their mouth-melting behaviour, i.e. the melting behaviour in the mouth, may be affected which in turn may affect the mouthfeel sensation of products containing thereof. Also, the water droplets dispersed throughout the fat phase of the W/O emulsion, which usually carry flavours or taste-enhancing components, may not effectively break in the mouth, influencing therefore the taste of a product containing such emulsion. The replacement of such emulsifiers in low-fat W/O emulsions with emulsifiers which help avoiding these problems may therefore bring a number of benefits such as optimal demulsification in the mouth and may enable the removal of E476 andE 471 from labelling.

Another method to stabilize an emulsion is known from WO 2013/003670, which utilizes an emulsifier composition comprising a blend of a lecithin and an additional emulsifier. However, the emulsifier composition of this publication may lack the emulsification power which makes it optimal for being used in producing a W/O emulsion, in particular a low-fat W/O emulsion.

Edible W/O emulsions used as dairy product substitutes are also known from EP 0 997 074 and EP 0 997 075, said emulsions utilizing an emulsifier comprising an alcohol-insoluble fraction of vegetable lecithin. M. Akhtar et al. (Food Colloids—Fundamentals of Formulation, ISBN 0-85404-850-2) also use a de-oiled fractionated lecithin which was phosphatidylcholine depleted to make W/O and W/O/W emulsions. The inventors observed that the properties of these known emulsions may be further improved.

Other methods to stabilise W/O emulsions include the use of polysaccharides such as hydro-colloids, e.g. starch, alginate, pectin, xanthan and carrageenan. However, with decreasing the fat content, these methods become increasingly ineffective in preventing phase separation and creaming, i.e. release of water during mechanical manipulation thereof, e.g. during spreading.

An object of the present invention may therefore be to provide a low-fat W/O emulsion which is the least possible affected by the above mentioned problems. A particular aim of the present invention may also be to provide a low-fat W/O emulsion having optimum stability at low and ambient temperatures. A more particular aim of the present invention may be to provide a low-fat W/O emulsion which spreads easily and shows good organoleptic properties.

SUMMARY OF THE INVENTION

It has been surprisingly found that one or more of the objectives indicated above may be achieved with a low-fat water-in-oil (W/O) emulsion comprising
(I) a fat phase in an amount of at most 60 wt % relative to the total weight of the emulsion;
(II) an aqueous phase dispersed within the fat phase; and (III) an emulsifier composition, said emulsifier composition comprising an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a weight ratio R of at most 65%, the ratio R being defined according to Formula 1:

$$R(\text{in }\%) = 100 \times \frac{PC + PI + PE + PA}{AI} \quad \text{Formula 1}$$

wherein PC+PI+PE+PA is the sum of the individual weights of the respective constituents of the AI component and AI is the total weight of the AI component.

DESCRIPTION OF THE DRAWINGS

FIGS. 1.1 to 1.3 show an overall stability of low-fat W/O emulsions in accordance with the invention.

DETAILED DESCRIPTION

The invention relates to a low-fat W/O emulsion comprising a fat phase in an amount of at most 60 wt % relative to the total weight of the emulsion, an aqueous phase dispersed within the fat phase and an emulsifier composition, said emulsifier composition comprising an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a weight ratio R of at most 65%, the ratio R being defined according to Formula 1:

$$R(\text{in }\%) = 100 \times \frac{PC + PI + PE + PA}{AI} \quad \text{Formula 1}$$

wherein PC+PI+PE+PA is the sum of the individual weights of the respective constituents of the AI component and AI is the total weight of the AI component.

The inventors observed that the inventive emulsion has an optimum balance between emulsion's stability and mouthfeel. While being optimally stable, the inventive emulsion may also have an agreeable mouth-melting behaviour. It was observed that products containing such emulsions have an optimum break down in the mouth whereby the content of the aqueous phase, e.g. taste and flavour components, is optimally released. Without being bound to any theory, the inventors believe that it is the amount of PC which mainly influences the emulsion's stability, the carefully chosen ratios of PC, PA. PE and PI which mainly influences the spreadability and/or mouthfeel thereof. Hence, to inventors' knowledge it is for the first time that such optimal balance was achieved by carefully choosing the specific amounts and the specific ratios of the AI and of the PC, PA, PE and PI.

In particular, the inventive emulsion is stable at ambient temperatures as well as at low temperatures, in particular at temperatures between 1 and 10° C., more in particular between 4 and 6° C., and may provide a food product containing thereof with at least one of the following features: (i) optimum spreadability for a broad range of temperatures; (ii) reduced and even no water release in particular during its spreading; (iii) optimum melting in the mouth; (iv) reduced "sticky" sensation in the mouth; (v) minimal unpleasant taste or off-taste; (vi) preferably devoid of acyl-glycerols, e.g. polyglycerol polyricinoleate (PGPR) and/or mono- or di-glycerides; (vii) containing a reduced amount of hardstock fat and for certain applications being free of hardstock fat; and (viii) easy and cheap to produce.

The emulsifier composition used in accordance with the invention comprises an Acetone-Insoluble (AI) component, which is understood as the component comprising a group of constituents obtained upon mixing the emulsifier composition with acetone, decanting and extracting the acetone in accordance with the method presented herein below in the "Methods for measurement" section. Preferably the AI component is in a weight ratio of at least 40% relative to the total weight of the emulsifier composition, more preferably at least 50%, most preferably at least 60%. Preferably, the AI is at most 80%, more preferably at most 70%. Preferably, the AI component is between 50 and 70 wt % of the total weight of the emulsifier corn position.

As used herein, PC, PA, PE and PI are constituents of the emulsifier composition, which are insoluble in acetone and may be commonly referred to as phospholipid fractions. It is herein understood that the individual phospholipid fractions may contain modified and non-modified fractions. Examples of modified phospholipid fraction include hydrolyzed PC, PA, PE and Pt, i.e. lyso-derivatives thereof, hereinafter denoted as L-PC, L-PA, L-PE and L-PI, respectively. Preferably, the emulsifier composition used in accordance with the invention contains modified phospholipid fractions, in particular hydrolyzed fractions (i.e. lyso-derivatives of said phospholipid fractions), in a total amount of less than 20 wt %, more preferably less than 15 wt % relative to their non-modified counterparts. Most preferably, the emulsifier composition used in accordance with the invention is free of hydrolyzed phospholipid fractions, wherein by the term "free" is herein meant that said emulsifier composition contains a total weight of hydrolyzed phospholipid fractions of at most 5000 ppm, more preferably at most 3000 ppm, even more preferably at most 1000 ppm, most preferably at most 500 ppm. The inventors observed that said emulsifier composition has good flavor and optimum emulsification power even in the absence of modified phospholipid fractions, and thus qualifying as a "clean label" composition.

Preferably, the characteristic ratio R of the emulsifier composition contained by the inventive emulsion is at most 63%, more preferably at most 61%, most preferably at most 60%. Preferably, R is between 30% and 63%, more preferably between 40% and 61%, even more preferably between 45% and 59.5%, most preferably between 50% and 59%.

Preferably, the amount of PC in the emulsifier composition contained by the inventive emulsion is at most 15.0%, more preferably at most 13.0%, even more preferably at most 10.5%, most preferably at most 8.5%, most preferably at most 7.5%. Preferably said amount of PC is at least 3.0%, more preferably at least 4.5%, most preferably at least 6.0%. Preferably the amount of PC is between 3.0% and 15.0%, more preferably between 5.0% and 13.0%, even more preferably between 6.0% and 10.0%, most preferably between 7.0% and 8.5%. Preferably, said PC contains, relative to its amount, at most 15.0% L-PC, more preferably at most 10,0% L-PC, most preferably at most 5.0% L-PC.

Preferably the PA in the emulsifier composition is in an amount of at most 10%, more preferably at most 6.5%, even more preferably at most 4.5%, yet even more preferably at most 4.0%, yet even more preferably at most 3.5%, most preferably at most 3% relative to the total weight of the emulsifier composition. Preferably, said amount of PA is at least 0.1%, more preferably at least 1.0%, even more preferably at least 1.5%, even more preferably at least 2.3%, most preferably above 2.5%. Preferably, said PA contains, relative to its amount, at most 20.0% L-PA, more preferably at most 10.0% L-PA, most preferably at most 5.0% L-PA.

Preferably the PE in the emulsifier composition is in an amount of at most 30%, more preferably at most 20%, even more preferably at most 16.8%, yet even more preferably at most 16.5%, most preferably at most 16.3% relative to the total weight of the emulsifier composition. Preferably, said amount of PE is at least 1.0%, more preferably at least 4.5%, even more preferably at least 6.0%, even more preferably at least 9.5%, most preferably at least 13%. Preferably, said PE contains, relative to its amount, at most 20.0% L-PE, more preferably at most 10.0% L-PE, most preferably at most 5.0% L-PE.

Preferably the PT in the emulsifier composition is in an amount of at most 30.0%, more preferably at most 25.0%, most preferably at most 20.0%, relative to the total weight of the emulsifier composition. Preferably, said amount of PI is at least 5.0%, more preferably at least 8.0%, even more preferably at least 10,0%, most preferably at least 12.0%. Preferably, said PI contains, relative to its amount, at most 20,0% L-PI, more preferably at most 10.0% L-PI, most preferably at most 5.0% L-P.

Preferably, the emulsifier composition used in accordance with the invention has a ratio $P_1:P_2$ of from 1:1 to 1.7:1; wherein $P_1$ is defined as the weight ratio of phospholipids components according to Formula 2:

$$P_1 = \frac{PC + LPC + PI + PA}{PE}; \quad \text{Formula 2}$$

and $P_2$ is defined as the weight ratio of phospholipids components according to Formula 3:

$$P_2 = \frac{PC + LPC + PI}{PE + PA}. \quad \text{Formula 3}$$

Preferably, $P_1$ is in the range of from 1.20 to 2.60; more preferably in the range from 1.30 to 2.25; most preferably in the range from 1.40 to 1.80. Preferably, $P_2$ is in the range of from 0.60 to 1.60; more preferably in the range from 0.80 to 1,40; most preferably in the range from 1.00 to 1.20. In one embodiment, the emulsifier composition used according to present invention preferably has a phospholipid $P_1$ value in the range of from 1.40 to 1.80 and a $P_2$ value in the range of from 1.03 to 1.18; most preferably in the range from 1.07 to 1.16. It was observed that for such values of $P_1$ and $P_2$, the emulsifying composition had a high emulsifying capacity, with good stabilising properties.

Preferably, the emulsifier composition used in accordance with the invention has a ratio $P_3$ of at most 0.70, more preferably at most 0.60, most preferably at most 0.50, wherein $P_3$ is defined according to Formula 4:

$$P_3 = \frac{PE + PI + PA}{AI}. \quad \text{Formula 4}$$

Preferably, the ratio $P_3$ is at least 0.10, more preferably at least 0.2, most preferably at least 0.3. Preferably, $P_3$ is between 0.38 and 0.50, more preferably between 0.40 and 0.49, even more preferably between 0.43 and 0.48.

The inventors surprisingly observed that optimum results were obtained at certain ratios of the phospholipids in the emulsifier composition used in accordance with the invention. in particular the inventors observed that optimum emulsification power was obtained when the emulsifier composition used in accordance with the invention has a ratio PC/PE of preferably at most 1.30, more preferably at most 1.00, even more preferably at most 0.80, most preferably at most 0,50. Preferably said PC/PE ratio is at least 0.01, more preferably at least 0.1, most preferably at least 0.2.

Preferably, the emulsifier composition used in accordance with the invention has a ratio PE/AI (in %) of at least 14.0%, more preferably at least 16.0%, even more preferably at least 18.0%, most preferably at least 20.0%. Preferably said PE/AI ratio is at most 40.0%, more preferably at most 35.0%, most preferably at most 30.0%.

Preferably, the emulsifier composition used in accordance with the invention has a ratio PI/AI (in %) of at least 14.0%, more preferably at least 16.0%, most preferably at least 18.0%. Preferably said PI/AT ratio is at most 35.0%, more preferably at most 30.0%, most preferably at most 25.0%.

Preferably, the emulsifier composition used in accordance with the invention has a ratio $P_5$ of at most 4.30, more preferably at most 4.10, most preferably at most 3.90, wherein $P_5$ is defined according to Formula 5:

$$P_5 = \frac{PC}{PE} + \frac{PC}{PA} + \frac{PC}{PI}; \quad \text{Formula 5}$$

Preferably, the ratio $P_5$ is at least 0.50, more preferably at least 1.00, most preferably at least 1.50. Preferably, $P_5$ is between 0.50 and 4.30, more preferably between 1.00 and 4.10, even more preferably between 1.50 and 3.90.

In a preferred embodiment, the emulsifier composition used in accordance with the invention comprises an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a weight ratio R of at most 65%, the ratio R being defined according to Formula 1 above, wherein the PA is in an amount of at most 10%, wherein the PE is in an amount of at most 30%, wherein the PI is in an amount of at most 30.0% and wherein the ratio $P_3$ is between 0.38 and 0.50. Preferred values of the AI, PC, PE, PI, PA, R and $P_3$ are given above and will not be repeated herein since they are fully applicable for this preferred also.

In another preferred embodiment, the emulsifier composition used in accordance with the invention comprises an Acetone-insoluble (AI) component containing a Phosphatidyl Choline (PC), a Phosphatidyl inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a weight ratio R of at most 65%, the ratio R being defined according to Formula 1 above, wherein the PA is in an amount of at most 10%, wherein the PE is in an amount of at most 30%, wherein the PI is in an amount of at most 30.0% and wherein the ratio PC/PE is at most 1.30. Preferred values of the AI, PC, PE, PI, PA, R and for the ratio PC/PE are given above and will not be repeated herein since they are fully applicable for this embodiment also.

In another preferred embodiment, the emulsifier composition used in accordance with the invention comprises an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a weight ratio R of at most 65%, the ratio R being defined according to Formula 1 above, wherein the PA is in an amount of at most 10%, wherein the PE is in an amount of at most 30%, wherein the PI is in an amount of at most 30.0% and wherein the ratio PE/AI is least 14.0%. Preferred values of the AI, PC, PE, PI, PA, R and for the ratio PE/AI are given above and will not be repeated herein since they are fully applicable for this embodiment also.

In another preferred embodiment, the emulsifier composition used in accordance with the invention comprises an Acetone-insoluble (AI) component containing a. Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a weight ratio R of at most 65%, the ratio R being defined according to Formula 1 above, wherein the PA is in an amount of at most 10%, wherein the PE is in an amount of at most 30%, wherein the PI is in an amount of at most 30.0% and wherein the ratio PI/AI is least 14.0%. Preferred values of the AI, PC, PE, PI, PA, R and for the ratio PI/AI are given above and will not be repeated herein since they are fully applicable for this embodiment also.

In a preferred embodiment, the emulsifier composition used in accordance with the invention comprises an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a weight ratio R of at most 65%, the ratio R being defined according to Formula 1 above, wherein the PA is in an amount of at most 10%, wherein the PE is in an amount of at most 30%, wherein the PI is in an amount of at most 30.0% and wherein the ratio $P_5$ is at most 4.30, Preferred values of the AI, PC, PE, PI, PA, R and $P_5$ are given above and will not be repeated herein since they are fully applicable for this embodiment also.

The emulsifier composition used in accordance with the invention stabilizes the inventive emulsion and may influence its organoleptic properties. The amount of emulsifier composition is preferably at least 0.001 wt % based on the total weight of the emulsion, more preferably at least 0.01 wt %, most preferably at least 0.1 wt %, Said amount is preferably at most 20 wt %, more preferably at most 15 wt %, even more preferably at most 10 wt %, even more preferably at most 5 wt %, even more preferably at most 3 wt %, most preferably at most 1 wt %.

The emulsifier composition may be used as a liquid or as a powder. When used as a liquid, said emulsifier composition may contain the AI component dispersed in a liquid phase which is soluble in acetone. The liquid phase of the emulsifier composition may contain triglycerides as the main component but may also contain monoglycerides, diglycerides, glycerol, glycolipids and fatty acids.

The emulsifier composition used in accordance with the invention may be produced by a known fractionation process such as the one disclosed for example in WO 2014/066623 and WO 2014/066632, both disclosures being incorporated herein by reference.

The inventive emulsion contains a fat phase. The fat phase of W/O emulsions is typically a mixture of fat which is liquid (the oil part in the fat phase) and a fat which is solid (usually referred to as hardstock fat) at ambient temperature. The hardstock fat contains crystals which stabilize the W/O emulsion by forming a lattice (or network) of crystals throughout the liquid fat and containing spaces including the aqueous phase droplets, therefore preventing the droplets to coalesce and separate from the fat phase. The fat phase of the inventive emulsion may thus contain a liquid fat (usually referred to in the art as liquid oil or simply oil); a solid fat; or a mixture of said liquid fat and said solid fat. The terms 'liquid oil' and 'liquid fat' may be used interchangeably within the context of the present invention. The term 'liquid oil' encompasses both triglyceride oils and diglyceride oils. Examples of the liquid oils that may be used in the present invention include without limitation various modified or unmodified vegetable and animal oils, such as palm oil, avocado oil, mustard oil, flaxseed oil, grape oil, peanut oil, coconut oil, olive oil, thistle oil, grape kernel oil, sesame oil, soybean oil, sunflower oil, linseed oil, cotton oil, rapeseed oil, low erucic rapeseed oil (Canola), corn oil, rice oil, safflower oil, kapok oil, sesame oil, evening primrose oil, fish oil and train (whale) oil and mixtures thereof. Examples of solid fats include without limitation various modified or unmodified vegetable and animal solid fats, such as butter fat and chocolate fat, e.g. cacao butter, shea butter, sal butter; chicken fat; beef tallow; milk fat; lard and mixtures thereof. The above fats and oils may be modified by subjecting them to various treatments, examples thereof including without limitation hydrogenation, fractionation and/or trans-esterification.

Preferably, the amount of the fat phase in the inventive emulsion is at most 50 wt %, more preferably at most 40 wt %. In a preferred embodiment, the amount of fat phase is at most 30 wt %, more preferably at most 25 wt %, In another embodiment, the amount of the fat phase is between 30 wt % and 60 wt %, more preferably between 35 wt % and 55 wt %, most preferably between 40 wt % and 45 wt %. In yet another embodiment, the amount of fat phase is between 5 wt % and below 30 wt %, more preferably between 10 wt % and 28 wt %, most preferably between 15 wt % and 25 wt %.

In a preferred embodiment, the inventive emulsion contains between 30 and 60 wt % fat based on the total weight of the emulsion, more preferably between 33 wt % and 50 wt % fat, most preferably between 35 wt % and 45 wt % fat and further it contains an amount of emulsifier composition of between 0.01 and 1.90 wt %, more preferably between 0.10 and 1.85 wt %, most preferably between 0.30 and 1.80 wt % based on the total weight of the emulsion.

In another preferred embodiment, the inventive emulsion contains between 5 wt % and 29 wt % fat based on the total weight of the emulsion, more preferably between 10 wt % and 27 wt % fat, most preferably between 15 wt % and 25 wt % fat and further it contains an amount of emulsifier composition of between 2.0 and 20 wt %, more preferably between 2.5 and 10 wt %, most preferably between 3.0 and 8 wt % based on the total weight of the emulsion.

In one embodiment, the fat phase of the inventive emulsion contains at most 10 wt % of hardstock fat based on the total weight of the emulsion, more preferably at most 5 wt %, most preferably at most 1 wt % hardstock fat. Hardstock fat according to the present invention is defined as a fat that has a solid content at 30° C. (N30) of more than 25 wt %, preferably more than 50 wt %, most preferably more than 80 wt %. It was surprisingly found that the inventive emulsion having reduced amount of fat and reduced amount of hardstock fat, is ambient stable without the need of using additional acylglycerols as emulsifiers. To determine the solid fat content of hardstock, the method presented in US 2009/0029025 A1 (paragraphs [0055]-[0063]) can be used.

In another embodiment, the inventive emulsion is an edible emulsion. In case the edible inventive emulsion contains a solid fat, ideally the solid fat content is chosen such that it melts or dissolves optimally at in-mouth conditions; otherwise the product may have a heavy and/or waxy mouthfeel. An important indicator is the temperature at which a W/O emulsion breaks up. Preferably, the inventive emulsion breaks up at in-mouth conditions to provide a good oral response. Furthermore, the overall organoleptic impression should be smooth and preferably no perceivable grains should be present upon ingestion as this may result in what is generally known as a 'sandy', 'grainy' and/or 'lumpy' mouthfeel.

The inventive emulsion also contains an aqueous phase. The aqueous phase of the inventive emulsion is dispersed as droplets within the continuous fat phase. It was observed that the emulsifier composition used in accordance with the invention helps in effectively stabilizing and uniformly dispersing said droplets throughout the fat phase. The aqueous phase may comprise further ingredients examples thereof including without limitation salt, colours, sweeteners, anti-oxidants, acidifying agents, flavouring agents, vitamins, dietary fibers, texturizing fibers and/or preservatives. The aqueous phase may also comprise gelling or non-gelling proteins, like for example vegetable and/or dairy proteins. An example of a gelling protein is gelatine. The aqueous phase may also comprise commonly known gelling, non-gelling and/or thickening agents, examples thereof including without limitation polysaccharides like starches, vegetable gums and pectin. Preferably the gelling and/or thickening agent are selected from the group consisting of physically or chemically modified starch, gelatine, alginate, pectin, maltodextrin, fibers and combinations thereof. An example of fibers are citrus fibers. The aqueous phase may have a pH set to a desired value in order to e.g. influence acidic or basic taste impression and/or to influence microbial stability. Preferably, the pH of the aqueous phase is between 4.0 and 5.0.

To aid in homogeneously distributing the droplet of the aqueous phase in the continuous fat phase, the droplet size distribution $D_{3,3}$ of the dispersed aqueous phase is preferably less than 20 µm, more preferably from 2 µm to 10 µm. To determine the $D_{3,3}$ the method presented in US 2009/0029025 A1 (paragraph [0052]) can be used.

Preferably, the inventive emulsion is substantially free of additional emulsifiers, in particular acylglycerol-based emulsifiers, which herein are understood as molecules containing esters formed from glycerol and fatty acids. Particular examples of acylglycerols include without limitation polyglycerol polyricinoleate (PGPR), monoglycerides and diglycerides.

In a first preferred embodiment, the inventive emulsion is substantially free of PGPR. By substantially free is herein understood that the inventive emulsion contains less than 2000 ppm PGPR based on its total weight, even more preferably less than 1000 ppm. Most preferably the inventive emulsion is completely free of PGPR, i.e. the content of PGPR is zero ppm. The present inventors have surprisingly identified that the emulsifier composition used in accordance with the invention has significant emulsifying properties and can be used successfully to replace PGPR in low-fat W/O emulsions. This replacement may be complete. The use of said emulsifier composition in food applications could lead to significant benefits for the customer including but not being limited to: (i) optimal mouthfeel; and (ii) enable the removal of E476 from labelling.

PGPR is a food grade emulsifier consisting of a hydrophilic group containing polyglycerol and a hydrophobic group containing interesterified ricinoleic fatty acids. PGPR is tipically made by mixing polyglycerol with interesterified ricinoleic fatty acids obtained by e.g. heating castor oil fatty acids above 200° C.

Polyglycerols are substances consisting of oligomer ethers of glycerol. Polyglycerols are usually prepared from an alkaline polymerization of glycerol at elevated temperatures. The processes for making polyglycerols are well known to the person skilled in the art and can be found for example in "*Emulsifiers in Food Technology*", Blackwell Publishing, edited by R J Whithurst, page 110 to 130. The polyglycerol component of the PGPR is typically a mixture of polyglycerols of varying degrees of polymerization. It will be understood that the degree of polymerization can vary. In one embodiment, the polyglycerol used to form the polyglycerol ester of a polymerized fatty acid is a mixture of polyglycerols selected from diglycerol, triglycerol, tetraglycerol, pentaglycerol, hexaglycerol, heptaglycerol, octaglycerol, nonaglycerol and decaglycerol. In one preferred embodiment triglycerol is the most abundant polyglycerol in the mixture of polyglycerols. In one preferred embodiment tetraglycerol is the most abundant polyglycerol in the mixture of polyglycerols. In one preferred embodiment the mixture of polyglycerols contains triglycerol in an amount of 30-50 wt % based on the total weight of polyglycerois and contains tetraglycerol in an amount of 0-30 wt % based on the total weight of polyglycerols. In one embodiment, the polyglycerotl is considered to be a diglycerol. In one embodiment, the polyglycerol is considered to be a triglycerol. In one embodiment, the polyglycerol is considered to be a tetraglycerol. In one embodiment, the polyglycerol is considered to be a pentaglycerol. In one embodiment, the polyglycerol is considered to be a hexaglycerol. In one embodiment, the polyglycerol is considered to be a heptaglycerol. In one embodiment, the polyglycerol is considered to be an octaglycerol. In one embodiment, the polyglycerol is considered to be a nonaglycerol. In one embodiment, the polyglycerol is considered to be a decaglycerol. In one embodiment, the polyglycerol moiety shall be composed of not less than 75% of di-, tri- and tetraglycerols and shall contain no more than 10% of polyglycerols equal to or higher than heptaglycerol. Polyglycerols may be linear, branched or cyclic in structure. Typically, all three types of polyglycerol structure are present in the composition of the present invention.

Fatty acids are well known in the art. They typically comprise an "acid moiety" and a "fatty chain". The properties of the fatty acid can vary depending on the length of the fatty chain, its degree of saturation, and the presence of any substituents on the fatty chain. The fatty acid used to prepare PGPR is ricinoleic acid. Ricinoleic acid is a chiral molecule and may be prepared by any suitable means known to the person skilled in the art, e.g. from a castor oil via hydrolyzation and distillation.

In a second preferred embodiment, the inventive emulsion is substantially free of mono- and/or diglycerides, i.e. mono or di esters of fatty acids and glycerol. Most preferably, the inventive emulsion is completely free of mono- and diglycerides. "Substantially free" and "completely free" bear herein the same meaning as that defined for PGPR.

In a third preferred embodiment, the inventive emulsion is substantially free, more preferably completely free, of PGPR, monoglycerides and diglycerides.

In a preferred embodiment, the inventive emulsion comprises:
  (i) between 1 and about 60 wt % of fat phase, more preferably between 10 and 50 wt %, most preferably between 20 and 40 wt %;
  (ii) from 40 to 99% by weight of one or more aqueous phases, preferably from 50 wt % to 90 wt %; most preferably from 60 wt % to 80 wt %;
  (iii) based on the total weight of the emulsion, from 0.001 to about 10 wt %, preferably between 0.01 and 8 wt %, most preferably between 0, 1 and 6 wt % of the emulsifier composition; and
  (iv) optionally sweeteners, proteins, taste and flavour components, vitamins, colorants, anti-oxidants, bulking agents, further co-emulsifiers, solid structuring agents, viscosity modifiers, in concentrations adding up to 100 wt %.

Preferably, the inventive emulsion further comprises one or more viscosity modifiers. Suitable viscosity modifiers include polysaccharides such as starches and gums, examples of said gums including without limitation gelatin, agar agar, pectin, alginic acid, sodium alginate, potassium alginate, beta-glucans, carrageenan, glucomannan, guar gum, gum ghatti, gum tragacanth, karaya gum, tara gum, fenugreek gum, xanthan, maltodextrins and/or locust bean gum. The term "gums", herein refers to all gum polysaccharides of various origins, e.g. from algae, bacteria or fungi.

The inventive emulsion may further contain solid structuring agent particles. Suitable solid particles may be platelets having a preferred average thickness of between 0.01 and 0.5 µm and agglomerates thereof. Preferably, said platelets are edible lipids. Such particles are known for example from EP 1 865 786. In another embodiment, said solid particles are starch granules, wherein said starch granules or a portion thereof are situated at the interface between the two phases, i.e. the aqueous phase and the fat phase. The starch granules preferably have a small granular size in the range of approximately 0.2-20 µm, preferably 0.2-8 µm, more preferably 0.2-4 µm, most preferably 0.2-1 µm. Preferably, the amount of added starch granules in the inventive emulsion corresponds to approximately 0.005-70 vol % of the total emulsion. The amount of added starch granules is preferably determined by the coverage of a water droplet and coverage should be more than 10%. A method of calculating an optimum amount of starch granules in the inventive emulsion as well as the size of said granules can be found in WO 2012/082065, incorporated herein in its entirety by reference.

The inventive emulsion is desirably stable under storage at temperatures from 1° C. up to ambient temperatures. This storage stability may be determined for example by storing a sample of the product in a plastic container at 4, 6, 10, 15, 20 and 25° C. for up to 20 weeks, more preferably up to 24 weeks, most preferably up to 26 weeks. An unstable emulsion may release in time oil (also known as oiling out) and/or water, effects known as phase separation. The extent of phase separation depends on the storage temperature and storage time. In case of the inventive emulsions, the presence of phase separation was determined after the storage time by visual examination (without the aid of a microscope) of the product's surface. Storage stable products do not show a phase separation (no oiling out/no water release) upon storage at 25° C. for at least 10 weeks, preferably at least 26 weeks.

The invention further relates to a secondary emulsion comprising the inventive emulsion. The secondary emulsion may be for example, an oil-in-water-in-oil (O/W/O) emulsion, or a water-in-oil-in-water (W/O/W) emulsion. In the case of an oil-in-water-in-oil (O/W/O) emulsion, references to an aqueous phase will be understood to include the oil-in-water (O/W) phase, and references to the fat phase will be understood to refer to the bulk fat phase. In the case of a water-in-oil-in-water emulsion, references to the aqueous phase will be understood to refer to the discrete (innermost) water phase The inventive emulsions have the advantage that they can be manufactured with practically any known process for making W/O emulsions, e.g. the process of EP 0 997 074 or EP 0 997 075. It was observed that the process for making the inventive emulsions may use standard equipment.

According to one embodiment an aqueous phase is prepared comprising water soluble ingredients and separately a fat phase is prepared comprising fat phase ingredients and the aqueous phase and fat phase are mixed to obtain the inventive emulsion. The mixing of the fat phase and the aqueous phase is preferably carried out by using a series of common processing equipment, or unit operations. For example the use of a pin stirrer in combination with a scraped surface heat exchanger unit, optionally repeating these unit operations several times, is suitable for the preparation of the inventive emulsions.

According to another embodiment, the process for preparing the inventive emulsion, comprising the steps of:
  (a) contacting:
    (i) a fat phase containing the emulsifier composition used in accordance with the invention,
  with
    (ii) an aqueous phase; and
  (b) forming an emulsion wherein the fat phase provides a continuous phase and wherein the aqueous phase provides a dispersed phase.

The temperature of the aqueous phase and/or the fat phase may be raised in order to facilitate mixing, e.g. typically between 40 and 80° C., preferably between 50 and 60° C.

The invention further relates to various food products containing the inventive emulsion, examples thereof including spreadable food products, e.g. low-fat margarine; coatings, e.g. for frozen confections; light and low-fat mayonnaise type products; fillings; dips; sauces; toppings; meat-based products; batters and dairy-based products. It was observed that the inventive emulsion had a high versatility allowing using it in a wide variety of applications.

The above mentioned food products may contain a W/O emulsion, a W/O/W emulsion or an O/W/O emulsion.

A spreadable food product is defined as being easily spread at temperatures of between 4° C. and the ambient temperature, with a knife on a substrate such as bread, without tearing the substrate during spreading. A spreadable food product, hereinafter spread, according to the invention is low-fat and hence it provides fewer calories per serving. In addition to the inventive emulsion, the spread of the invention may further contain a starch, an alginate, a pectin, a maltodextrin or a combination thereof, to further optimize the mouthfeel of said spread. Preferred starches are starches of which at least 50 wt % is fully gelatinised. More preferably the starches at least 70 wt %, more preferred at least 80 wt %, even more preferred at least 90 wt % is fully gelatinised. The most preferred starch is a fully gelatinised starch. In the spread according to the invention, the aqueous phase preferably comprises a fully gelatinised starch selected from any of the main starch groups: wheat, tapioca, potato, rice, maize, waxy rice or waxy maize. The amount of starch in said spread depends somewhat on the type of chosen starch and is preferably from 0.2 to 10 wt %, more preferred from 0.7 to 7 wt %, most preferred from 1 to 5 wt %. It is immediately understood that although called spread, the product of the invention can be used in many other applications, examples thereof including without limitation bakery, in e.g. the making of pastry and dough. In one embodiment, the spread of the invention is an aerated spread having an overrun of preferably less than 10%, more preferably less than 5%. The overrun can be determined according to EP 2 442 665, the disclosure of which is herein incorporated by reference.

It was observed that a spread containing the inventive emulsion shows minimal and even no phase separation, i.e. release of oil and water, even if it is kept for a longer time, e.g. up to 20 weeks, more preferably up to 24 weeks, most preferably up to 26 weeks at ambient temperatures.

The invention further relates to a composition comprising an Acetone-Insoluble (AI) component containing a Phosphatidyl Choline (PC), a Phosphatidyl Inositol (PI), a Phosphatidyl Ethanolamine (PE) and a Phosphatidic Acid (PA), wherein the amount of the PC is at most 13% relative to the total weight of the composition and wherein the composition is characterized by a weight ratio R of at most 65%, the ratio R being defined according to Formula 1 presented above. Preferably, R of the inventive composition is at most 63%, more preferably at most 61%, most preferably at most 60%. Preferably, R is between 30% and 63%, more preferably between 40% and 61%, most preferably between 50% and 59%. Preferably the AI component is in a weight ratio of at least 40% relative to the total weight of the inventive composition, more preferably at least 50%, most preferably at least 60%. Preferably, the AI is at most 80%, more preferably at most 70%. Preferably, the AI component is between 50 and 70 wt % of the total weight of the inventive composition. The inventive composition preferably has a ratio $P_1:P_2$ of from 1:1 to 1.7:1; wherein $P_1$ and $P_2$ are defined above in Formulas 2 and 3, respectively. Preferably, the amount of PC in the inventive composition is at most 13.0%, more preferably at most 12.0%, even more preferably at most 10.5%, most preferably at most 8.5%, most preferably at most 7.5%. Preferably the amount of PC is between 5.0% and 13.0%, more preferably between 6.0% and 10.0%, most preferably between 7.0% and 8.5%. The inventive composition of the invention preferably has a ratio $P_3$ as defined in Formula 4 of at most 0.50. Said $P_3$ is preferably between 0.38 and 0.50, more preferably between 0.40 and 0.50. Preferably, the inventive composition comprises PA, PE, PI and/or the ratios PC/PE, PE/AI, PI/AI and/or $P_5$ within the ranges and preferred embodiments as defined hereinabove which are equally applicable herein. The preferred ranges for PA, PE and for the ratios $P_1$, and $P_2$, defined hereinabove are equally applicable to the inventive composition and will not be repeated further herein.

The invention further relates to a composition comprising an Acetone-Insoluble (AI) component containing a Phosphatidyl Inositol (PI), a Phosphatidyl Ethanolamine (PE) and a Phosphatidic Acid (PA), wherein the composition is characterized by a weight ratio $P_3$ as defined in Formula 4 of between 0.45% and 0.50%. The preferred ranges for the AI, PA, PE, PT and PC contents and ratios R, $P_1$, $P_2$, $P_3$, PC/PE, PE/AI and PI/AI as presented hereinabove are equally suitable for this composition and thus will not be repeated further herein.

The compositions of the invention may be used as a liquid or as a powder. When used as a liquid, said compositions may contain the AI component dispersed in a liquid phase which is soluble in acetone. The liquid phase of the compositions may contain triglycerides as the main component but may also contain monoglycerides, diglycerides, glycerol, glycolipids and fatty acids.

The compositions of the invention may be produced by a process such as the one disclosed for example in WO 2014/066623 and WO 2014/066632 by choosing an optimal extraction process. The invention further relates to the use of said compositions as emulsifiers, in particular as W/O emulsifiers.

The invention further relates to food products, in particular those defined hereinabove, containing the compositions of the invention.

The invention is further presented with the help of the following examples and comparative experiments, without being however limited thereto.

Methods for Measurement

Spreadability is determined according to the following in house developed protocol: a flexible palette knife is used to spread a small amount of a spread sample onto a fat free paper/cardboard at fridge temperature (4 to 6° C.). The spreading of the sample is evaluated according to a standardized scaling. A score of (5) represents a homogeneous and smooth spread without any defects; a (4) refers to the same product but then with small remarks as slightly inhomogeneous or some vacuoles e.g grainy aspect; a (3) refers to the level where defects become more visible, like slightly loose moisture or increased grainy texture during spreading. A score of 3 is rather acceptable but requires further recipe and or process development. A score of (2) or (1) refers to unacceptable products, where most of the products will still have some spreading properties, but an unacceptable level of defects and mainly release of water.

Particle size measurement (D3,3) is performed with a low resolution NMR, Bruker Minispec; (as for example detailed in WO2013/0413326, pg. 8, paragraphs 15 to 25) The average water droplet size is expressed as D3,3. The occurrence of larger water droplets is expressed in the value of e^sigma, a higher value indicates the presences of larger droplets into the spread which could lead to water pockets into the matrix influencing stability and spreading. It has been experienced that e^sigma is preferably between 1 and 4.

Acetone insolubles were determined according to Lange R., Fiebig H. J. (1999): Separation of Phospholipids, Standard Methods of DGF, Fett/Lipid 101: 77-79. This method is based on the solubility of lecithin components such as triglycerides, fatty acids, sterols, and other acetone-soluble components, and the insolubility of the phospholipids and glycophospholipids in acetone under the test conditions. The latter are termed acetone insolubles (AT). AI may also be determined in accordance with AACC international Method 58-35.01—"*Acetone-Insoluble Lecithin*", however the former method is preferred.

Phosholiid Composition: The phospholipid composition, i.e. the amounts of PC, PA, PI and PE and their hydrolysed fractions was determined using a liquid-chromatographic method applied on emulsifier compositions having an AI set to 60% relative to the total weight of the emulsifier composition. AI amount can be adjusted by adding (or extracting e.g. with acetone) the necessary amount of the acetone soluble part (mainly triglycerides) of said composition in order to bring the AI amount to 60%. The identification and quantification of the various phospholipid components may conveniently be executed by different methods, including thin-layer chromatography (TLC), high performance liquid chromatography (HPLC) and $^{31}$P nuclear magnetic resonance spectroscopy ($^{31}$P-NMR) for the phospholipids only. Suitable methods are disclosed in London E., Feigenson G. W. (1979): Phosphorous NMR Analysis of Phospho lipids in Detergents, J. Lipid Res. 20: 408-412; Aitzetmüller K. (1984): HPLC and Phospholipids, Part I: General Considerations, Fette, Seifen, Anstrichm. 86: 318-322; and Aloisi J. D., Sherma J., Fried B. (1990): Comparison of Mobile Phases for Separation and Quantification of Lipids by One-Dimensional TLC and Preadsorbent High Performance Silica Gel Plates, J. Liq. Chromatogr. 13:3949-3961.

EXAMPLES AND COMPARATIVE EXPERIMENTS

Examples 1-5

A number of 5 different compositions were made following a method similar to that of WO 2014/066632 wherein the extraction step was adjusted to yield the optimum amounts of phospholipid components. The % amounts of the various phospholipid components together with their AI amounts is presented in Table 1a. The ratios R, $P_1$-$P_5$, PC/PE, PE/AI and PI/AI are presented in Tables 1b and 1c. A standard soy-lecithin (TOPCITHIN® 200) was used as emulsifier for the Comparative Experiment.

TABLE 1a

| | Emulsifier composition | | | | |
|---|---|---|---|---|---|
| | AI (%) | PA (%) | PC (%) | PE (%) | PI (%) |
| Composition 1 | 67.4 | 3.91 | 5.25 | 14.15 | 15.36 |
| Composition 2 | 67.2 | 2.9 | 7.4 | 16.3 | 12.9 |
| Composition 3 | 66.8 | 3.21 | 6.06 | 15.7 | 13.8 |
| Composition 4 | 67.0 | 3.17 | 6.59 | 15.35 | 13.86 |
| Composition 5 | 63.4 | 3.89 | 6.27 | 14.04 | 13.5 |
| TOPCITHIN ® 200 | 64.2 | 2.19 | 15.68 | 12.76 | 8.18 |

TABLE 1b

| | Emulsifier composition | | | | |
|---|---|---|---|---|---|
| | R | $P_1$ | $P_2$ | $P_3$ | $P_4$ |
| Composition 1 | 57% | 1.75 | 1.16 | 0.50 | 6.37 |
| Composition 2 | 59% | 1.45 | 1.08 | 0.48 | 4.34 |
| Composition 3 | 58% | 1.49 | 1.07 | 0.49 | 5.40 |
| Composition 4 | 58% | 1.60 | 1.16 | 0.48 | 4.91 |
| Composition 5 | 59% | 1.71 | 1.12 | 0.50 | 5.01 |
| TOPCITHIN ® 200 | 60% | 2.13 | 1.67 | 0.36 | 1.48 |

TABLE 1c

| | Emulsifier composition | | | |
|---|---|---|---|---|
| | PC/PE | PE/AI | PI/AI | $P_5$ |
| Composition 1 | 0.37 | 21.0% | 22.8% | 2.06 |
| Composition 2 | 0.45 | 24.3% | 19.2% | 3.58 |
| Composition 3 | 0.39 | 23.5% | 20.7% | 2.71 |
| Composition 4 | 0.43 | 22.9% | 20.7% | 2.98 |
| Composition 5 | 0.45 | 22.1% | 21.3% | 2.52 |
| TOPCITHIN ® 200 | 1.23 | 19.9% | 12.7% | 10.31 |

The phospholipid compositions of Tables 1a-c were used as the emulsifier composition to manufacture W/O emulsions.

Examples 6-9 (W/O Emulsions Containing 40 wt % Fat Phase)

The ingredients used and their amounts are presented in Table 2. Composition 2 was used as the emulsifier composition.

All water soluble ingredients were added to water at 50-60° C. with the use of an adequate dispersing equipment to form the water phase. All oil soluble ingredients were blended together at around 50-60° C. (above the melting point of the fat and eventually the melting point of the emulsifier) to form the fat phase.

The complete water phase was added to the fat phase under agitation until a homogenous emulsion was obtained. This liquid emulsion was being further processed by means of a scrapped surface heat exchanger in order to start crystallisation and create the optimal texture thereof.

The above described process is well known to the skilled person and is usually referred as the Votator process.

Examples 10-12 (W/O Emulsions Containing 25 wt % Fat Phase)

The ingredients used and their amounts are presented in Table 3. Composition 2 was used as the emulsifier composition.

The same process as the one used in Examples 6-9 was used to manufacture the 25 wt % fat containing emulsions also.

TABLE 2

| | Emulsion 0 | Emulsion 1 | Emulsion 2 | Emulsion 3 |
|---|---|---|---|---|
| | | % | | |
| Hardstock fat | 16.00 | 16.00 | 16.00 | 16.00 |
| Liquid oil | 23.60 | 23.40 | 23.30 | 23.50 |
| PGPR | 0 | 0 | 0 | 0 |
| Dimodan U/J | 0.40 | 0.40 | 0.20 | 0.00 |
| Emulsifier composition | 0.00 | 0.20 | 0.50 | 0.50 |
| Flavours/color | traces | traces | Traces | traces |
| TOTAL FAT PHASE | 40 | 40 | 40 | 40 |
| Satialgine LSP 263 | 0.60 | 0.60 | 0.60 | 0.60 |
| Salt | 0.50 | 0.50 | 0.50 | 0.50 |
| Citric acid | 0.10 | 0.10 | 0.10 | 0.10 |
| Potassium sorbate | 0.10 | 0.10 | 0.10 | 0.10 |
| Water | 58.70 | 58.70 | 58.70 | 58.70 |
| TOTAL AQUEOUS PHASE | 60 | 60 | 60 | 60 |

TABLE 3

|  | Emulsion 4 | Emulsion 5 (%) | Emulsion 6 |
|---|---|---|---|
| Hardstock fat | 10.00 | 10.00 | 10.00 |
| Liquid oil | 13.80 | 11.90 | 11.5 |
| Palsgaard PGPR 4175 | 0.40 | 0.00 | 0.00 |
| Dimodan U/J | 0.60 | 0.60 | 0.00 |
| Emulsifier composition | 0.20 | 2.5 | 3.5 |
| TOTAL FAT PHASE | 25 | 25 | 25 |
| Satialgine LSP 263 | 0.80 | 0.80 | 0.80 |
| C*DryLight MD 01970 | 2.00 | 2.00 | 2.00 |
| Salt | 0.50 | 0.50 | 0.50 |
| Citric acid | 0.10 | 0.10 | 0.10 |
| Potassium sorbate | 0.10 | 0.10 | 0.10 |
| Water | 71.50 | 71.50 | 71.50 |
| TOTAL AQUEOUS PHASE | 75 | 75 | 75 |

Spreadability and Stability Measurements

Spreadability and the stability of the W/O emulsions of Tables 2 and 3 were measured as described in Methods for Measurement section at different time intervals from day 0 of production to 3 months after production. The samples were stored at fridge temperature (4 to 6° C.). The "Spreadability rating" was used as a measure for the overall stability of the W/O emulsion, higher rankings indicating better products. Ranking after week 1 are presented in Table 4.

FIGS. 1.1 to 1.3 show the overall stability of the W/O emulsions 1 to 3, respectively, containing a diglycerides and/or composition 2 as emulsifier (▲) and containing comparative as emulsifier (●), respectively. The overall stability of emulsion 0 (containing only diglycerides (DIMODAN) as emulsifier) is indicated in the figures with the square marker (■).

Droplet size (D3,3 and E^sigma) was measured 1 day after production. Results are presented in Table 5.

TABLE 4

|  | Emulsion 1 | Emulsion 2 | Emulsion 3 |
|---|---|---|---|
| Composition 2 | 5 | 5 | 5 |
| Comparative | 5 | 5 | 0 |

TABLE 5

|  | Composition 2 | Comparative |
|---|---|---|
| D(3.3) μm |  |  |
| Emulsion 1 | 4.8 | 4.5 |
| Emulsion 2 | 6.4 | 5.3 |
| Emulsion 3 | 7.5 | 16 |
| E^sigma |  |  |
| Emulsion 1 | 2.12 | 1.94 |
| Emulsion 2 | 2.6 | 2.07 |
| Emulsion 3 | 3.3 | 2.7 |

It was observed that the emulsifier compositions of the invention enabled the manufacturing of the above W/O emulsions and provide said emulsions with satisfactory stability performance. In comparison, when the comparative emulsifier was used, there were conditions when low fat W/O emulsions were not possible to manufacture due to stability problems.

It was further observed that the use of the inventive emulsifier compositions of Table 1 enables the manufacturing of spreads free of PGPR and/or mono- or di-glycerides, which during spreading thereof maintain their homogeneity and smooth appearance with few if any defects occurring therein.

The invention claimed is:

1. A low-fat water-in-oil (W/O) emulsion comprising a fat phase in an amount of at most 40 wt % relative to the total weight of the emulsion, an aqueous phase dispersed within the fat phase and an emulsifier composition, said emulsifier composition comprising an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a weight ratio R of at most 65%, the ratio R being defined according to Formula 1:

$$R(\text{in }\%) = 100 \times \frac{PC + PI + PE + PA}{AI} \qquad \text{Formula 1}$$

wherein PC+PI+PE+PA is the sum of the individual weights of the respective constituents of the AI component and AI is the total weight of the AI component; and
wherein the emulsifier composition is characterized by a ratio $P_3$ of at most 0.50, wherein $P_3$ is defined according to Formula 4:

$$P_3 = \frac{PE + PI + PA}{AI}. \qquad \text{Formula 4}$$

2. The emulsion according to claim 1 wherein the AI component is in a weight ratio of at least 40% relative to the total weight of the emulsifier composition.

3. The emulsion according to claim 1 wherein R is at most 63%.

4. The emulsion according to claim 1 wherein the amount of PC is at most 15.0.

5. The emulsion according to claim 1 wherein the PA is in an amount of at most 10%.

6. The emulsion according to claim 1 wherein the PE is in an amount of at most 30.

7. The emulsion according to claim 1 wherein the PI is in an amount between 10% and 30%.

8. The emulsion according to claim 1 wherein the emulsifier composition is characterized by a ratio $P_5$ of at most 4.30, wherein $P_5$ is defined according to Formula 5:

$$P_5 = \frac{PC}{PE} + \frac{PC}{PA} + \frac{PC}{PI}. \qquad \text{Formula 5}$$

9. Food products containing the emulsion of claim 1, said products being chosen from the group of products consisting of spreadable food products, coatings, light and low-fat mayonnaise type products, fillings, dips, sauces, toppings, meat-based products, batters and dairy-based products.

10. A water-in-oil emulsion composition comprising an Acetone-Insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the composition and wherein the composition is characterized by a weight ratio R of at most 65%, the ratio R being defined according to Formula 1:

$$R(\text{in }\%) = 100 \times \frac{PC + PI + PE + PA}{AI}; \quad \text{Formula 1}$$

and having a ratio $P_3$ as defined in Formula 4:

$$P_3 = \frac{PE + PI + PA}{AI} \quad \text{Formula 4}$$

of at most 0.50.

11. The composition of claim 10 wherein the amount of PC is at most 13.0.

12. The composition of claim 10, which is free of hydrolyzed phospholipids.

13. The emulsion according to claim 1 wherein the AI component is in a weight ratio of at least 50% relative to the total weight of the emulsifier composition.

14. The emulsion according to claim 1 wherein the AI component is in a weight ratio of at least 60% relative to the total weight of the emulsifier composition.

* * * * *